US00PP34795P2

(12) United States Plant Patent
Halladin

(10) Patent No.: US PP34,795 P2
(45) Date of Patent: Dec. 6, 2022

(54) ***PICEA PUNGENS* TREE NAMED 'INHOOPMO'**

(50) Latin Name: *Picea pungens*
Varietal Denomination: 'INHoopMo'

(71) Applicant: Early Morning LLC, Boring, OR (US)

(72) Inventor: Paul H. Halladin, Boring, OR (US)

(73) Assignee: EARLY MORNING LLC, Boring, OR (US)

( * ) Notice: Subject to any disclaimer, the term of this patent is extended or adjusted under 35 U.S.C. 154(b) by 0 days.

(21) Appl. No.: 17/875,912

(22) Filed: Jul. 28, 2022

(51) Int. Cl.
*A01H 5/00* (2018.01)
*A01H 6/00* (2018.01)

(52) U.S. Cl.
USPC ..... Plt./213
CPC ..... *A01H 6/00* (2018.05)

(58) Field of Classification Search
USPC ..... Plt./213
CPC ..... A01H 5/00
See application file for complete search history.

*Primary Examiner* — Kent L Bell
(74) *Attorney, Agent, or Firm* — Weatherly IP Solutions, LLC; Barbara Campbell

(57) ABSTRACT

A new and distinct variety of *Picea pungens* tree having a large, narrow conical shaped tree, all propagations develop orthotropic leader growth, and intense silver-blue colored foliage, as disclosed.

3 Drawing Sheets

Genus and species: *Picea pungens.*
Denomination: 'INHoopMo'.

BACKGROUND

'INHoopMo' is a new and distinct variety of *Picea pungens*. 'INHoopMo' originated from a controlled cross conducted in May 2001 in a greenhouse in Boring, Oreg. of the female *Picea pungens* parent 'Hoopsii' (unpatented) and the male *Picea pungens* parent 'Montgomery' (unpatented). The seeds from this cross germinated in May 2002.

'INHoopMo' was selected and first asexually propagated in January 2009 in Boring, Oreg. via grafting onto an unnamed *Picea abies* rootstock (unpatented).

'INHoopMo' reproduces true to type in successive generations since 2009 of asexual reproduction via grafting onto an unnamed *Picea abies* rootstock (unpatented).

SUMMARY

The following are the most outstanding and distinguishing characteristics of this new variety when grown under normal horticultural practices in Boring, Oreg.

1. Large, narrow conical shaped tree
2. All propagations develop orthotropic leader growth; and
3. Intense silver-blue colored foliage.

DESCRIPTION OF THE PHOTOGRAPHS

This new *Picea pungens* tree is illustrated by the accompanying photographs which show the plant's overall plant habit including form and foliage. The photographs are of a 10-year-old tree grown outdoors in Boring, Oreg. and were taken in June 2022 under cloudy conditions. The colors shown are as true as can be reasonably obtained by conventional photographic procedures.

DETAILED DESCRIPTION

Figure 1:
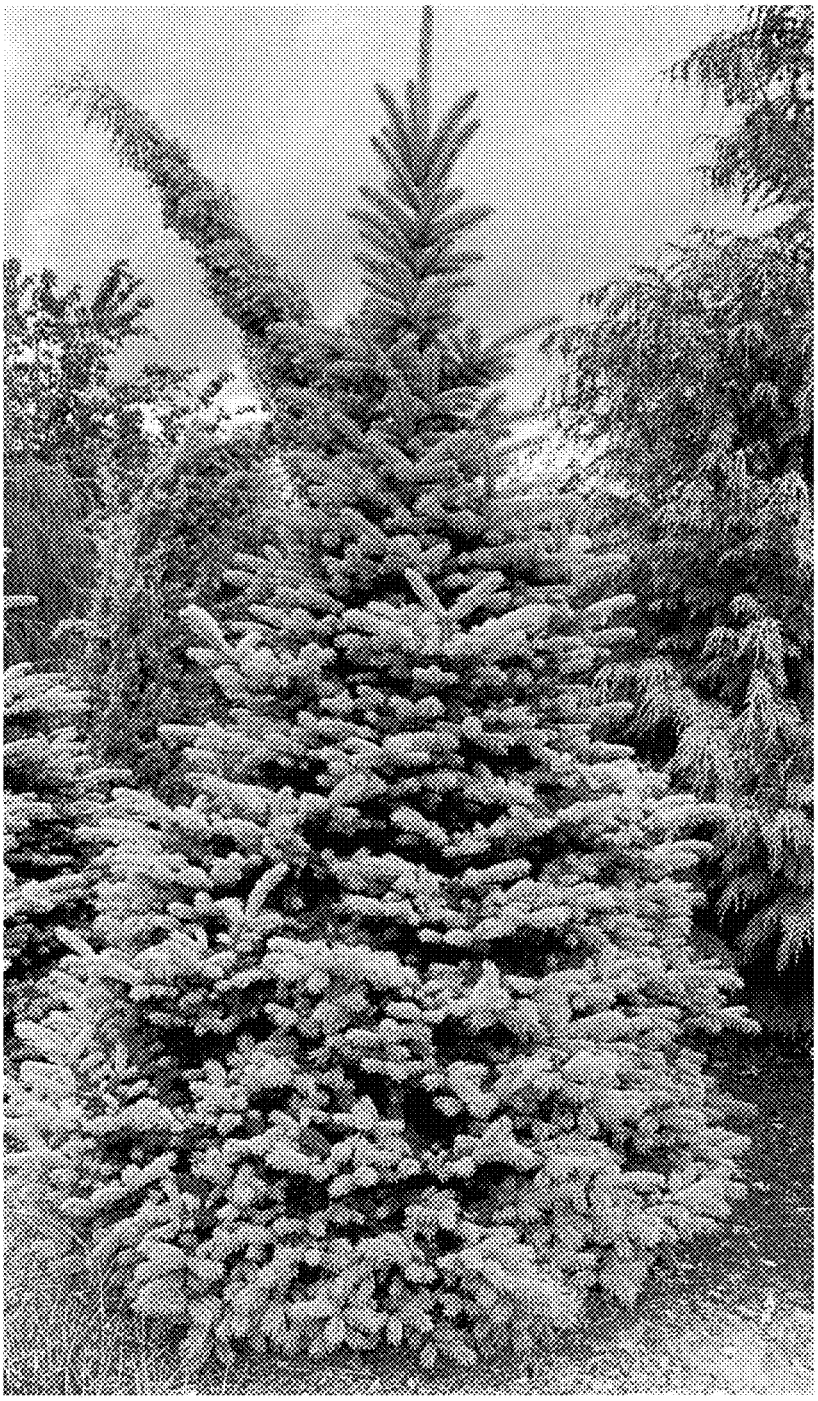
FIG. 1 shows the overall form of the whole tree of 'INHoopMo'.
Figure 2:
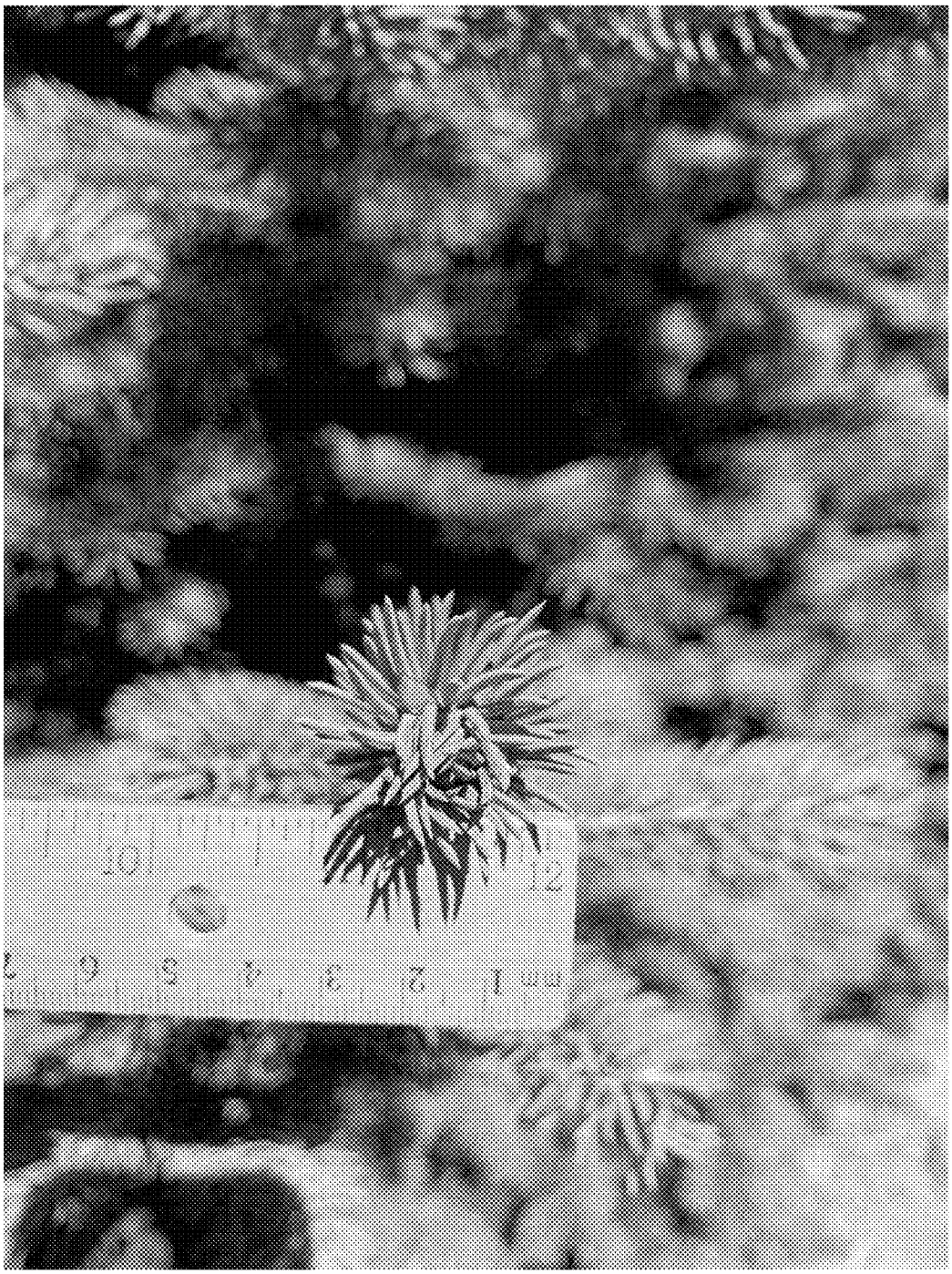
FIG. 2 shows a close-up of the buds and needles or leaves of the tree of FIG. 1.
Figure 3:
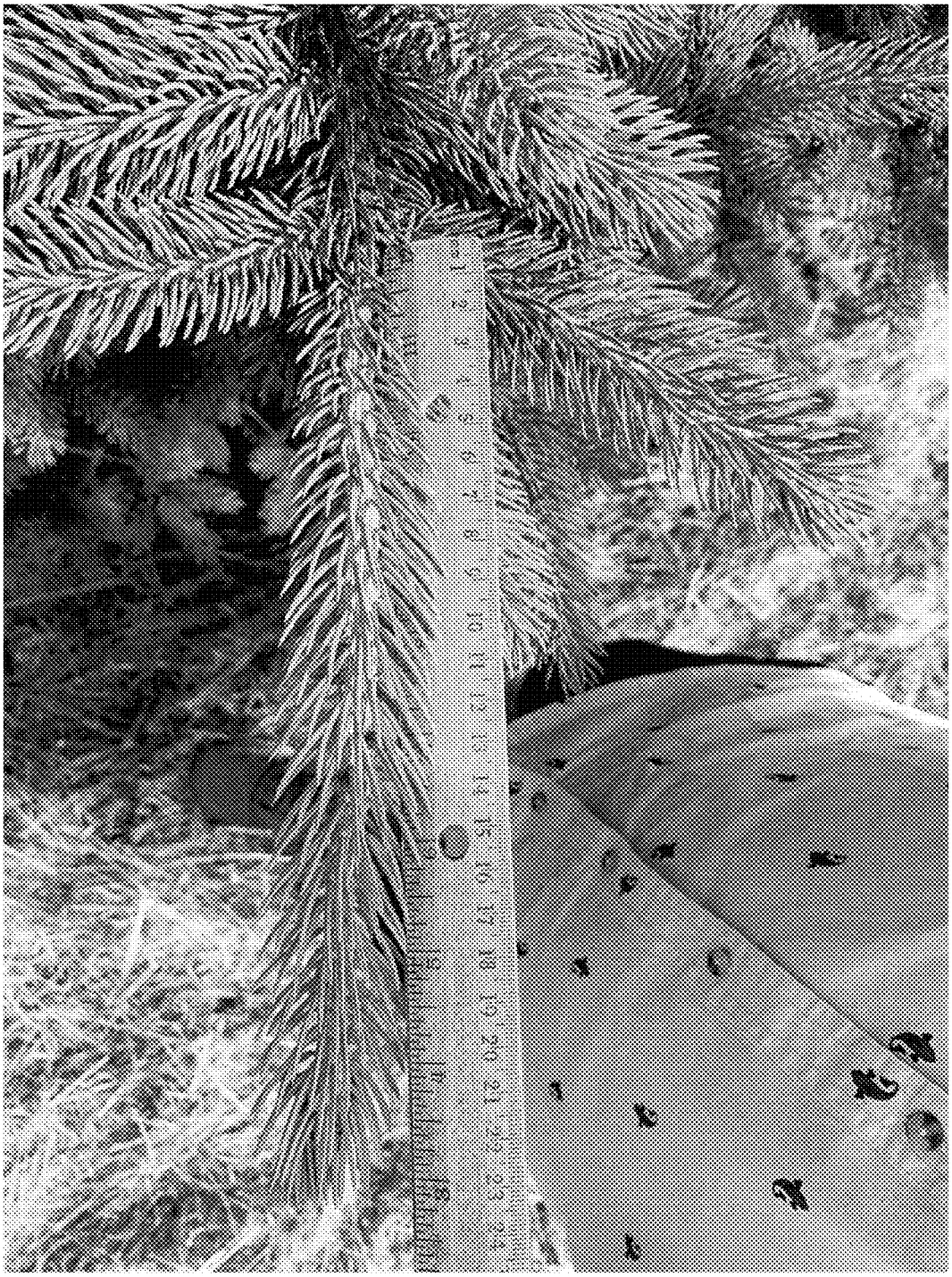
FIG. 3 shows a close-up of the terminal branch shoot of the tree of FIG. 1.

The following detailed descriptions set forth the distinctive characteristics of 'INHoopMo'. The data which define these characteristics were collected outdoors in Boring, Oreg. in June 2022 on 10-year-old trees in Boring, Oregon. Color references are to The R.H.S. Colour Chart of The Royal Horticultural Society of London (R.H.S.) 2001, except where general terms of ordinary dictionary significance are used.

Classification:
- *Family.*—Pinaceae.
- *Botanical.*—*Picea pungens.*
- *Denomination.*—'INHoopMo'.

Tree:
- *Type.*—Evergreen conifer.
- *Shape.*—Narrow conical.
- *Growth and branching habit.*—Large compact tree, single flush, with uniform branching pattern; no staking required; straight leader.
- *Propagation type.*—Grafting onto an unnamed *Picea abies* rootstock (unpatented).
- *Height (from soil line).*—250 cm at 10 years.
- *Width (horizontal plant diameter).*—145 cm at 10 years.
- *Length of terminal 1-year shoots.*—30.0 cm to 40.0 cm.
- *Length of subterminal 1-year shoots.*—15.0 cm to 20.0 cm.
- *Diameter of trunk.*—14.0 cm at 10 years.
- *Temperature tolerance or zones.*—USDA Zones 2 to 8.

Leaves (needles):
- *Arrangement.*—Radial, single.
- *Quantity of leaves/needles per terminal one-year branch shoot.*—490 to 500.

*Quantity of leaves/needles per subterminal one-year branch shoot.*—200 to 300.
*Shape*.—Needle-like, acicular.
*Apex*.—Acute.
*Base*.—Attenuate, attached to leaf peg.
*Margin*.—Entire, smooth.
*Leaf length, terminal shoot*.—Basal: 1.0 cm to 1.5 cm; Medial: 2.5 cm to 3.0 cm.
*Distal*.—1.5 cm to 2.0 cm.
*Width*.—0.2 cm.
*Texture*.—Smooth and covered with waxy layer.
*Pubescence*.—Absent.
*Mature leaf color for both upper and lower surfaces*.—RHS 122D (Blue-Green).
*Mature leaf color when wax rubbed off*.—RHS 189A (Greyed-Green).
*Petioles*.—Leaves are sessile on a short peg.

Buds: Buds are currently in the developmental stage and changing in characteristic. Buds are typical in size, color, and shape of the species.

Cones: No male or female cones have been observed to date.

Disease/pest resistance: No specific disease or pest resistance has been observed to date.

COMPARISON WITH PARENTAL AND COMMERCIAL LINES

Table 1 shows a comparison of the differences between 'INHOOPMO' and the commercial *Picea pungens* tree 'Fat Albert' (unpatented).

TABLE 1

| Comparison with Commercial Line | | |
|---|---|---|
| Characteristic | 'INHoopMo' | 'Fat Albert' |
| Shape | Narrow conical | Wide conical |
| Size, height × width at 10-years-old | 250 cm × 145 cm | 290 cm × 190 cm |

TABLE 1-continued

| Comparison with Commercial Line | | |
|---|---|---|
| Characteristic | 'INHoopMo' | 'Fat Albert' |
| Mature needle/leaf color | RHS 122D (Blue-Green) | RHS 130D (Green) |

Table 2 shows a comparison of differences between 'INHoopMo' and the parental lines.

TABLE 2

| Comparison with Parental Lines | | | |
|---|---|---|---|
| Characteristic | 'INHoopMo' | Female parent 'Hoopsii' | Male parent 'Montgomery' |
| Shape | Narrow conical | Irregular conical | Irregular flattened mound as an immature tree and wide conical as a mature tree |
| Branch growth type | Orthotropic | Plagiotropic | Plagiotropic |
| Growth habit | Large and compact; uniform branching; no staking required; straight leader | Large open tree; staking and pruning required for tree-like habit | Dwarf compact tree; flattened mound when immature and wide-conical when mature |
| Growth rate cm/year | 30 cm to 40 cm | 35 cm to 45 cm | 10 cm to 20 cm |
| Size, height × width at 10-years-old | 250 cm × 145 cm | 230 cm × 135 cm | 90 cm × 105 cm |
| Mature needle/leaf color | RHS 122D (Blue-Green) | RHS 112C (Blue-Green) | RHS 122B (Blue-Green) |

I claim:

1. A new and distinct variety of *Picea pungens* tree designated 'INHoopMo' as illustrated and described herein.

* * * * *